United States Patent [19]
Holland et al.

[11] 3,985,893
[45] Oct. 12, 1976

[54] METHOD FOR TREATING CARDIAC INSUFFICIENCY WITH ANTIBIOTIC A-23187

[75] Inventors: Donald R. Holland; Mitchell I. Steinberg, both of Indianapolis, Ind.

[73] Assignee: Eli Lilly and Company, Indianapolis, Ind.

[22] Filed: Oct. 29, 1974

[21] Appl. No.: 518,556

[52] U.S. Cl. ............................................. 424/272
[51] Int. Cl.² ......................................... A61K 31/42
[58] Field of Search ................................... 424/272

[56] References Cited
OTHER PUBLICATIONS

J. Amer. Chem. Soc., 96, 1932 (1974), M. O. Cheney et al.

Ann. N.Y. Acad. Sci., 227, pp. 412–418, Feb. 1974.

S. W. Shaffer et al., Biochem. Pharmacol. 23, pp. 1609–1617, June 1974.

Primary Examiner—James O. Thomas, Jr.
Assistant Examiner—Daren M. Stephens
Attorney, Agent, or Firm—William B. Scanlon; Everet F. Smith

[57] ABSTRACT

A method for enhancing the contractile force of mammalian heart muscle which comprises administering an effective amount of antibiotic A-23187, a divalent cation ionophore.

3 Claims, No Drawings

METHOD FOR TREATING CARDIAC INSUFFICIENCY WITH ANTIBIOTIC A-23187

BACKGROUND OF THE INVENTION

This invention relates to a method for treating cardiac insufficiency in warm-blooded mammals. In particular it relates to a method for enhancing the contractile force of mammalian cardiac muscle which comprises administering an effective amount of the antibiotic A-23187.

The stimulation of cardiac muscle in clinical situations producing cardiogenic shock, for example following myocardial infarction or in congestive heart failure, is clinically achieved by the administration of inotropic agents such as isoproterenol or other known cardioactive agents. Some of these agents act by releasing endogenous norepinephrine which in turn stimulates the heart muscle. Others, e.g., isoproterenol, act as agonists of β-receptors. Each of these mechanisms of action carries with it undesirable side reactions necessitating careful clinical observation. For example, the release of endogenous norepinephrine causes an increase in peripheral resistance which in turn places an additional undesirable burden on the heart.

There is a continuing need for more effective positive inotropic agents which do not act through release of endogenous norepinephrine or which are not agonists of β-receptors.

DESCRIPTION OF THE INVENTION

This invention provides a method for enhancing the contractile force of mammalian heart muscle which comprises the administration of an effective dose of the ionophoric antibiotic A-23187.

The antibiotic employed in the method of this invention is arbitrarily referred to as antibiotic A-23187.

The antibiotic is produced by culturing the microorganism *Streptomyces chartreusis* Calhoun and Johnson NRRL 3882 under submerged aerobic fermentation conditions as described in copending U.S. application Ser. No. 434,312, filed Jan. 17, 1974, which is a continuation-in-part application of application Ser. No. 237,532 filed Mar. 23, 1972 now abandoned. The antibiotic A-23187 has been previously described by R. L. Hamill et al., *Abstracts*, 12th Interscience Conference on Antimicrobial Agents and Chemotherapy, Atlantic City, N.J., September 26–29, 1972, page 65. Antibiotic A–23187 is represented by the following structural formula elucidated by M. O. Cheney et al., J. Amer. Chem. Soc., 96, 1932 (1974).

mass spectroscopy and X-ray analysis and is in agreement with the above structure.

In the above formula, the dotted bonding lines indicate that the bonded group is located below the plane of the ring to which it is attached. The spikes indicate that the attached groups are positioned above the plane of the ring.

In addition to its antibiotic activity, A-23187 is a known ionophore which specifically binds divalent cations, notably $Ca^{2+}$ [P. W. Reed, *Fed. Proc. Amer. Soc. Exp. Biol.*, 31, 432 (1972)]. The antibiotic has also demonstrated the ability to increase the movement of calcium ions across cell membranes.

The positive inotropic effect of A-23187 is demonstrated by standard tests employing isolated guinea pig left atria in a suitable tissue bath. At concentrations between about $3 \times 10^{-7}$ and $10^{-4}$ molar, A-23187 increased the force of contraction and the rate of tension development in isolated guinea pig left atria at 35° C. in Chenoweth-Koelle buffered bath solution. The increases in the force of contraction and the rate of tension development induced by A-23187 at a concentration of $10^{-4}$ molar were 75 percent and 60 percent, respectively, of those increases induced in the test by norepinephrine at its maximum effective concentration.

When guinea pigs were pretreated with 5 mg./kg. of reserpine, i.p., 24 hours before the experiment, the inotropic response of the isolated atria to A-23187 was not affected. Further, when propranolol was added to the buffered tissue bath at a concentration of about $3 \times 10^{-6}$ molar, prior to the addition of antibiotic A-23187, no effect on the inotropic activity of A-23187 was observed. In contrast, propranolol markedly depressed the response of the atria to norepinephrine.

These experiments strongly indicate that the positive inotropic effect of antibiotic A-23187 is not attributable to the release of endogenous norepinephrine or to activation of β-receptors. Although the mechanism by which A-23187 exerts its positive inotropic action has not been finally established, it appears likely that the known ability of A-23187 to transport calcium ions across cell membranes is implicated. The entry of calcium ions into the myoplasm may initiate the positive inotropic effect.

According to the practice of this invention, the antibiotic A-23187 is useful in enhancing the contractile force of mammalian heart muscle when administered in an effective non-toxic dose of between 25 mcg./kg. and about 500 mcg./kg. of body weight. The antibiotic is

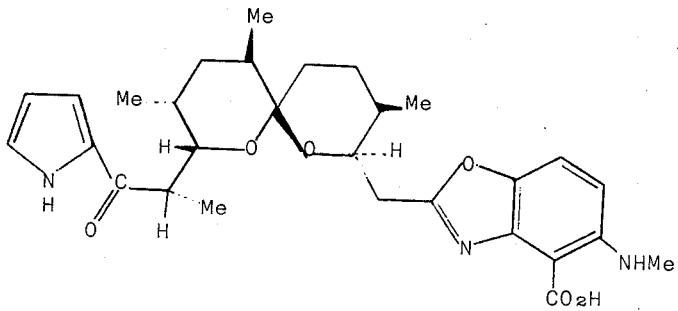

As shown, the antibiotic is a monocarboxylic acid containing an α-ketopyrrole and a benzoxazole moiety. The structure of A-23187 was determined by analysis of its nuclear magnetic resonance spectrum (nmr), administered parenterally, for example by intravenous infusion. A suitable method of administration is the drip method wherein the antibiotic is incorporated in a standard i.v. solution such as a dextrose solution.

A-23187 is desirably administered at doses below about 100 mcg./kg. until the desired enhancement of the contractile force is observed. Thereafter the amount of A-23187 administered can be regulated by the rate of infusion needed to maintain the desired response. As with the clinical administration of other inotropic agents, the dose of A-23187 administered may be varied in a given clinical case according to such factors as the individual's tolerance of A-23187, the nature of the heart's affliction, e.g., the extent of damage to the heart muscle, and the age and general physical condition of the patient.

The method of this invention comprising the use of the positive inotropic agent A-23187 can be used in a variety of clinical situations broadly classified as cardiogenic shock. Such conditions include, for example, myocardial infarction, congestive heart failure, and post-operative cardiogenic shock.

A-23187 is an effective inotropic agent in the free acid form or in the form of the calcium salt. The term "calcium salt" as used herein refers to A-23187 bound to calcium ion via chelation wherein two molecules of A-23187 cage a calcium cation.

Other salts of A-23187, for example the non-toxic pharmaceutically acceptable sodium and potassium salts, can be prepared by neutralizing the free acid form with a base such as sodium hydroxide, sodium carbonate, potassium hydroxide, or potassium carbonate. These salts can be useful in the preparation of pharmaceutical forms of A-23187.

Although the free acid form of A-23187 and the salt forms thereof are relatively insoluble in water solutions, effective doses can be obtained in the standard volumes of i.v. solutions, such as 5 percent dextrose, which are ordinarily employed clinically. Alternatively, a colloidal-like suspension in water can be used for administration. For example, a solution of A-23187 in dimethylsulfoxide when diluted with water or Ringer's solution forms an opalescent colloidal-like suspension.

A further method for preparing a soluble form of A-23187 or the calcium salt thereof comprises lyophilizing a nonaqueous solution (e.g., methanol) of A-23187 also containing in solution albumin. The lyophilized solid can then be dissolved in water to form a solution suitable for administration.

The following example illustrates the experimental method and techniques employed.

EXAMPLE 1

Female guinea pigs (250–350 g.) were stunned by a blow on the head and the left atrium was dissected. The tissue was mounted horizontally in a 5 ml. organ bath according to conventional techniques and the isometric tension was measured. (J. Levy, in "Methods in Pharmacology" [A. Schwarts, ed.] Vol. 1, p. 77, Meredith, New York [1971]). Resting tension was set at a value predetermined to give half maximal contractile tension. Stimuli of 1 msec duration were continuously delivered at a rate of 2 per second through bipolar silver electrodes.

In most experiments, a modified Chenoweth-Koelle buffer (saturated with 95 percent oxygen, 5 percent carbon dioxide) was used as the bath solution. The composition of this buffer was: NaCl, 120 mM; KCl, 5.6 mM; $CaCl_2$, 2.2 mM; $MgCl_2$, 2.2 mM; $NaHCO_3$, 25 mM; dextrose, 10 mM. The tissue was equilibrated at 35° C. for 30 to 60 minutes prior to the experiment. During equilibration the bathing solution was changed every 5 minutes. A-23187 was added to the organ bath as an opalescent, aqueous suspension made by diluting a stock solution of ionophore dissolved in 100 percent dimethylsulfoxide (DMSO). The maximal volume of DMSO added to the bath by this technique was 5 $\mu l$ and this produced no inotropic effect in four control experiments.

We claim:

1. The method of enhancing the contractile force of mammalian heart muscle in a warm blooded mammal which comprises administering parenterally an effective non-toxic dose of between approximately 25 mcg./kg. and 500 mcg./kg. of body weight of the antibiotic A-23187 free acid or the calcium salt thereof.

2. The method of claim 1 wherein the dose administered is below about 100 mcg./kg.

3. The method of claim 1 wherein the free acid form of A-23187 is administered.

* * * * *